United States Patent [19]

Looker

[11] Patent Number: 4,943,631
[45] Date of Patent: Jul. 24, 1990

[54] PROCESS FOR CEPHEM COMPOUNDS

[75] Inventor: Brian E. Looker, Greenford, England

[73] Assignee: Glaxo Group Limited, London, England

[21] Appl. No.: 141,192

[22] Filed: Jan. 6, 1988

Related U.S. Application Data

[63] Continuation-in-part of Ser. No. 781,744, Sep. 30, 1985, abandoned.

[30] Foreign Application Priority Data

Oct. 1, 1984 [GB] United Kingdom ................ 8424692

[51] Int. Cl.$^5$ ........................................... C07D 501/04
[52] U.S. Cl. .................................................. 540/222
[58] Field of Search ....................................... 540/222

[56] References Cited

U.S. PATENT DOCUMENTS

| | | | |
|---|---|---|---|
| 4,044,002 | 8/1977 | Hatfield | 540/222 |
| 4,394,503 | 7/1983 | Kamachi et al. | 540/225 |
| 4,406,899 | 9/1983 | Aburaki et al. | 540/222 |
| 4,457,929 | 7/1984 | Kamachi et al. | 540/222 |
| 4,500,526 | 2/1985 | Imae et al. | 540/226 |
| 4,525,473 | 6/1985 | Aburaki et al. | 540/222 |

FOREIGN PATENT DOCUMENTS 1591439  7/1983  United Kingdom .
2116180  2/1985  United Kingdom .

Primary Examiner—Nicholas S. Rizzo
Attorney, Agent, or Firm—Bacon & Thomas

[57] ABSTRACT

The present invention provides compounds of general formula (III)

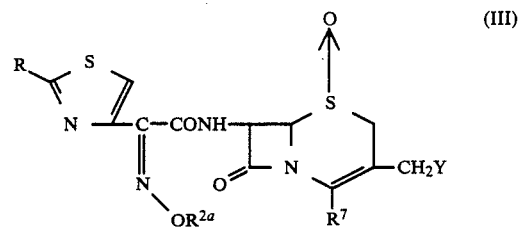

[wherein
R is an amino or protected amino group;
$R^{2a}$ is a straight or branched chain alkyl group containing from 1 to 4 carbon atoms, an allyl, but-2-enyl or but-3-enyl group, or is a group of formula

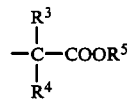

(wherein each of $R^3$ and $R^4$ is independently a hydrogen atom or a methyl or ethyl group, or $R^3$ and $R^4$ taken together with the carbon atom to which they are attached may be a cycloalkylidene group containing from 3 to 5 carbon atoms, and $R^5$ is a hydrogen atom or a carboxyl blocking group);
Y represents a 1-methyl-1-pyrrolidinium group and $R^7$ represents the group —COO$^-$ or —COOR$^6$, where $R^6$ is a hydrogen atom or a carboxyl blocking group] and salts thereof.

6 Claims, No Drawings

PROCESS FOR CEPHEM COMPOUNDS

This application is a continuation of application Ser. No. 781,744 filed Sept. 30, 1985, and now abandoned.

The invention also relates to the use of compounds of general formula (IIIA)

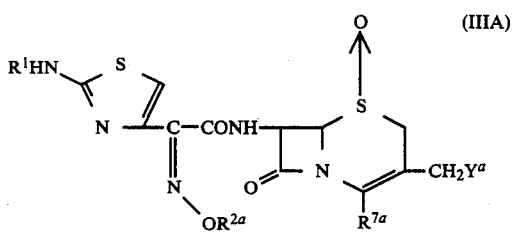

(wherein $R^1$ is a hydrogen atom or an amino protecting group;

$R^{2a}$ is as defined above;

$Y^a$ is a 1-pyrrolidino or 1-methyl-1-pyrrolidinium group and $R^{7a}$ represents the group —COOR$^6$, where $R^6$ is as defined above, or when $Y^a$ represents 1-methyl-1-pyrrolidinium, $R^{7a}$ may additionally represent the group —COO$^-$) or salts thereof for the preparation of cephalosporin antibiotics of general formula (I)

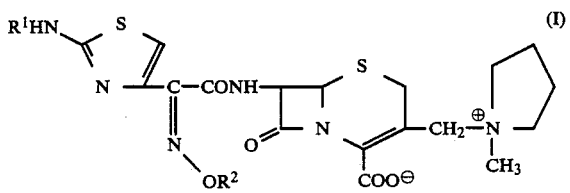

[wherein
$R^1$ is a hydrogen atom or an amino-protecting group, and
$R^2$ is a straight or branched chain alkyl group containing from 1 to 4 carbon atoms, an allyl, but-2-enyl or but-3-enyl group, or is a group of formula

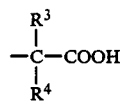

(wherein each of $R^3$ and $R^4$ is independently a hydrogen atom or a methyl or ethyl group, or $R^3$ and $R^4$ taken together with the carbon atom to which they are attached may be a cycloalkylidene group containing from 3 to 5 carbon atoms)]
non-toxic pharmaceutically acceptable salts and metabolically labile esters thereof and solvates of these compounds.

CHEMICAL COMPOUNDS

This invention is concerned with improvements in or relating to the preparation of cephalosporin compounds, in particular the preparation of a class of cephalosporin compounds possessing valuable antibiotic properties.

The cephalosporin compounds in this specification are named with reference to "cepham" after *J. Amer. Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, for example in the treatment of diseases caused by bacteria which are resistant to other antibiotics such as penicillin compounds and in the treatment of penicillin-sensitive patients. In many instances it is desirable to employ a cephalosporin antibiotic which exhibits activity against both Gram-positive and Gram-negative microorganisms and a significant amount of research has been directed to the development of various types of broad spectrum cephalosporin antibiotics.

U.K. Patent Application No.2116180 A describes cephalosporin compounds of formula (I)

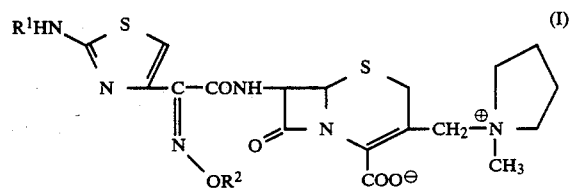

[wherein $R^1$ is a hydrogen atom or an amino-protecting group, and $R^2$ is a straight or branched chain alkyl group containing from 1 to 4 carbon atoms, an allyl, but-2-enyl or but-3-enyl group, or is a group of formula

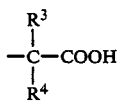

(wherein each of $R^3$ and $R^4$ is independently a hydrogen atom or a methyl or ethyl group, or $R^3$ and $R^4$ taken together with the carbon atom to which they are attached may be a cycloalkylidene group containing from 3 to 5 carbon atoms)] and non-toxic pharmaceutically acceptable salts and metabolically labile esters thereof and solvates of these compounds.

Preferably the compounds of formula (I) are synoximes essentially free from the corresponding anti-isomer. The syn-configuration is denoted structurally as

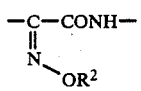

However, the compounds may exist as mixtures of the syn-isomer and its corresponding anti-isomer, denoted structurally as

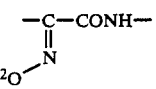

and such mixtures containing at least 90% of the syn isomer are also disclosed in UK Patent Application No. 2116180 A.

The compounds of formula (I) in which $R^1$ is a hydrogen atom are said to exhibit high antibacterial activity against various Gram-positive and Gram-negative bacteria, and to be useful in the treatment of bacterial infections in animals, including man. The preferred compounds of formula (I) disclosed are those in which $R^1$ is a hydrogen atom and $R^2$ is a methyl or ethyl group or a group of formula

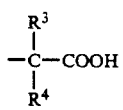

(wherein each of $R^3$ and $R^4$ is independently a hydrogen atom or a methyl group). In the most preferred compounds, $R^2$ is a methyl group or a group of formula

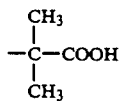

and the compound 7-[(Z)-2-methoxyimino-2-(2-aminothiazol-4-yl)acetamido]-3-[(1-methyl-1-pyrrolidinium)-methyl]-ceph-3-em-4-carboxylate is particularly preferred.

Two general processes for the preparation of the compounds of formula I as defined above and non-toxic pharmaceutically acceptable salts and metabolically labile esters thereof and solvates of these compounds are also described in UK Patent Application No.2116180 A.

Thus, one general process comprises 7-acylation of a compound of formula

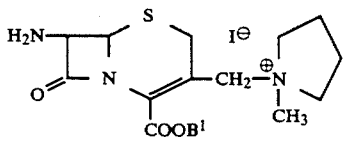

(wherein $B^1$ is hydrogen atom or a conventional carboxyl-blocking group) or an N-silyl derivative thereof, with an acylating agent corresponding to an acid of formula

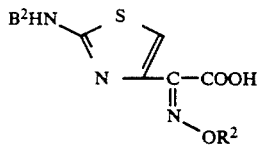

or

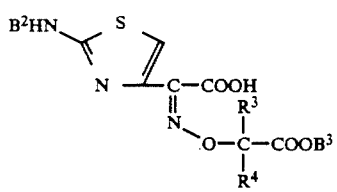

(wherein $B^2$ is a conventional amino-protecting group, $B^3$ is a conventional carboxyl-blocking group, and $R^2$, $R^3$ and $R^4$ are as defined above), e.g. the corresponding acid chloride, with subsequent removal of blocking and protecting groups. There are no working Examples, however, illustrating this method.

The second general process comprises a nucleophilic displacement reaction i.e. reaction of a compound of formula

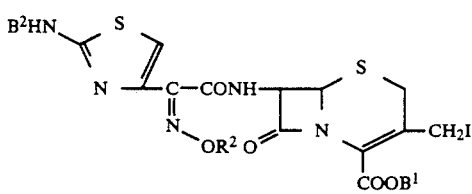

or

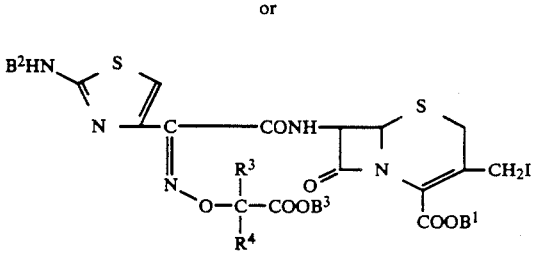

(wherein $R^2$, $R^3$ and $R^4$ are as defined above, $B^1$ and $B^3$ are conventional carboxyl-blocking groups, and $B^2$ is a conventional amino-protecting group) with N-methylpyrrolidine, with subsequent removal of blocking and protecting groups This is the only method exemplified It is found in practice, however, that the above nucleophilic displacement generally yields the products as a mixture of the desired ceph-3-em compounds with the undesired corresponding ceph-2-em compounds.

An important detrimental effect of this is that the overall yield of the desired $\Delta^3$ isomer is substantially reduced. Furthermore, a difficult purification step such as high pressure liquid chromatography is necessitated after the nucleophilic displacement reaction in order to remove the $\Delta^2$ isomer (and other impurities present). This purification method is impractical on a manufacturing scale.

Moreover, the yield of product (obtained as a mixture of $\Delta^3$ and $\Delta^2$ isomers) and the ratio of the isomers in the product are found to be extremely variable.

We have now found that, by employing a cephalosporin sulphoxide starting material in the nucleophilic displacement process and subsequently reducing the cephalosporin sulphoxide product, higher yields and purities of the desired compounds of formula (I) and derivatives thereof may be obtained, and isolation of the desired product is facilitated.

Although a nucleophilic displacement reaction using sulphoxide intermediates for the production of related compounds having a phenyl, furyl or thienyl group rather than the aminothiazolyl group present in formula (I) has been disclosed (see United Kingdom Patent No.1591439), it was not stated in relation to that series of compounds that use of sulphoxide intermediates provided the advantages in terms of increased yield and purity which we have found in the present instance.

Thus, in the first stage of the present reaction sequence, a compound of formula (II)

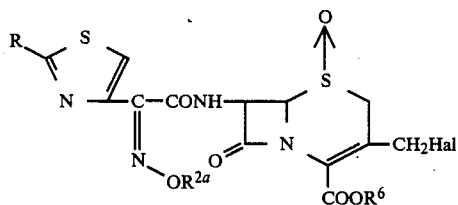 (II)

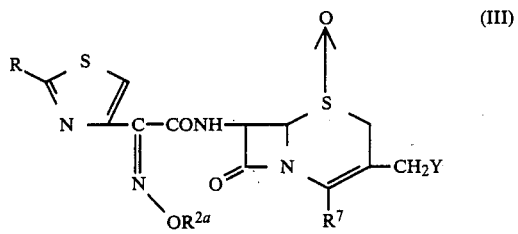 (III)

[wherein

R is an amino or protected amino group;

$R^{2a}$ is a straight or branched chain alkyl group containing from 1 to 4 carbon atoms, an allyl, but-2-enyl or but-3-enyl group, or is a group of formula

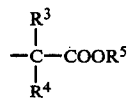

(wherein each of $R^3$ and $R^4$ is independently a hydrogen atom or a methyl or ethyl group, or $R^3$ and $R^4$ taken together with the carbon atom to which they are attached may be a cycloalkylidene group containing from 3 to 5 carbon atoms, and $R^5$ is a hydrogen atom or a carboxyl blocking group);

$R^6$ is a hydrogen atom or a carboxyl blocking group; and Hal is a halogen atom (e.g. a chlorine, bromine or iodine atom)], or a salt thereof, may be reacted with pyrrolidine or N-methylpyrrolidine to produce a compound of the general formula (IIIA)

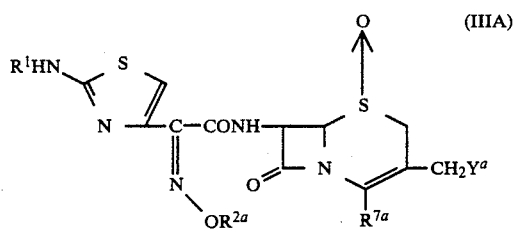 (IIIA)

(wherein $R^1$ and $R^{2a}$ have the above meanings, $Y^a$ represents a 1-pyrrolidino or 1-methyl-1-pyrrolidinium group and $R^{7a}$ represents the group —COOR$^6$, where $R^6$ is as defined above, or when $Y^a$ represents 1-methyl-1-pyrrolidinium, $R^{7a}$ may additionally represent the group —COO$^-$) or a salt thereof.

It will be appreciated that when $Y^a$ in the compound of formula (IIIA) above represents a 1- methyl-1-pyrrolidinium group and $R^7$ represents —COOR$^6$, the compound of formula (IIIA) will be associated with one or more anions, principally a halide ion (e.g. a chloride, bromide or iodide ion).

Compounds of general formula (III)

(wherein R and $R^{2a}$ are as defined above, Y represents a 1-methyl-1-pyrrolidinium group and $R^7$ represents the group —COO or —COOR$^6$, where $R^6$ is as defined above) and salts thereof are novel and constitute one feature of the present invention. The invention also includes the preparation of compounds of formula (III) and salts thereof by reaction of a compound of formula (II) or a salt thereof with pyrrolidine or N-methylpyrrolidine as described above, followed when pyrrolidine is used by reaction with a methylating agent.

The invention also includes the use of the compounds of formula (IIIA) as defined above and salts thereof in the preparation of compounds of formula (I) as hereinbefore defined and non-toxic pharmaceutically acceptable salts and metabolically labile esters thereof and solvates of these compounds. Such use may comprise:

(i) reduction of a 1-sulphoxide compound of formula (IIIA) or salt thereof to form the corresponding sulphide compound; and if necessary and/or desired:

(ii) methylation of a 3-(1-pyrrolidino)methyl compound to form the corresponding 3-(1-methyl-1-pyrrolidinium)methyl compound;

(iii) formation of a non-toxic salt and/or a non-toxic metabolically labile ester; and (iv) removal of any carboxyl blocking and/or amino protecting groups.

The above reactions, which may be effected in conventional manner and in any appropriate order, may be carried out optionally with or without previous isolation of the compound of formula (IIIA) or a salt thereof.

The term "salt" as used herein, unless the context dictates otherwise, refers to acid addition and base salts. For pharmaceutical use these salts will of course be physiologically acceptable non-toxic salts but other salts may find use, for example as intermediates and/or starting materials in the process of the invention. Acid addition salts include salts formed with organic and inorganic acids such as, for example, hydrochloric, hydrobromic, formic, nitric, sulphuric, phosphoric, methanesulphonic, p-toluenesulphonic, acetic or trifluoroacetic acid or other acids conventionally employed in the penicillin and cephalosporin art. Base salts include salts formed with organic and inorganic bases such as, for example, alkali metal salts (e.g. sodium or potassium salts) and alkaline earth metal salts (e.g. calcium salts), salts with amino acids (e.g. lysine or arginine salts) and salts formed with ammonia, triethylamine, procaine, phenethylbenzylamine, dibenzylethyldiamine or other bases conventionally employed in the penicillin and cephalosporin art.

Salts formed with acids and bases may be prepared in conventional manner by reacting a cephalosporin compound of formula (I), (II) or (IIIA) with an acid or base respectively The reaction of a compound of formula (II) or a salt thereof with pyrrolidine or N-methylpyrrolidine may conveniently be effected by maintaining the reactants in solution or suspension in a suitable medium at a moderate temperature, e.g. from −40° to +120° C., preferably from +10° to +50° C., and most preferably at or around ambient temperature.

The reaction is advantageously effected using from 1 to 30, preferably from 1 to 5 molar equivalents of pyrrolidine or N-methylpyrrolidine and is preferably carried out in an organic reaction medium and under anhydrous conditions. Solvents which may be used include ethers (e.g. acyclic ethers such as diethyl ether and diglyme and cyclic ethers such as dioxan or tetrahydrofuran); esters (e.g. ethyl acetate); amides (e.g. N,N-dimethylformamide and N,N-dimethylacetamide); hydrocarbons (e.g. benzene); lower (e.g. $C_{1-6}$) alkanols (e.g. t-butanol); ketones (e.g. acetone or methylisobutylketone); sulphoxides (e.g. dimethylsulphoxide); and sulphones (e.g. sulpholane), as well as mixtures of two or more such solvents. The reaction solvent is preferably an ether, such as tetrahydrofuran.

In the starting compound of formula (II) or salt thereof, $R^6$ and, if present, $R^5$, are preferably carboxyl blocking groups. It will be appreciated that the compound of formula (IIIA) will thus usually be obtained initially as a halide salt. This salt may, if desired, be subjected to one or more ion exchange reactions to obtain salts having other anions.

The reaction product may, if desired, be separated from the reaction mixture (which may contain, for example, unchanged pyrrolidine or N-methylpyrrolidine and other substances) by a variety of processes including precipitation, crystallisation, chromatography (e.g. column chromatography employing conventional adsorbents or ion-exchange chromotography), trituration, or the use of macroreticular resins. It is a characteristic of the present process, however, that the desired $\Delta^3$ isomer is obtained initially in relatively pure form and that subsequent purification is much easier than in the processes described in UK Patent Application No. 2116180 A.

When pyrrolidine is employed in the process, a compound of formula (IV)

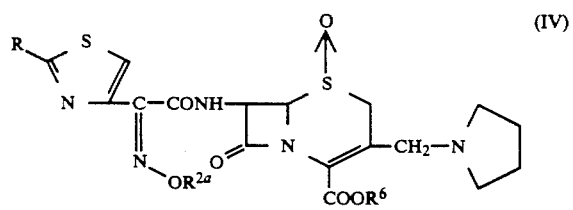

(wherein R, $R^{2a}$, and $R^6$ are as defined above) or a salt thereof is initially obtained, which may be converted by methylation to a compound of formula (III).

The methylation reaction is advantageously carried out using a compound of formula (IV) in which the group R is a protected amino group and $R^6$ and where present $R^5$ are carboxyl blocking groups, and with a methylating agent of formula $CH_3X$ [wherein X is a leaving group such as, for example, a halogen atom (e.g. an iodine, chlorine or bromine atom) or a hydrocarbylsulphonate (e.g. mesylate or tosylate) group] or with dimethylsulphate. Iodomethane or dimethylsulphate are preferred as the methylating agent.

The methylation is preferably carried out at a temperature from 0° to 60° C., advantageously from 20° to 30° C. Where the methylating agent is liquid under the reaction conditions (as, for example, in the case of iodomethane), the methylating agent itself may serve as a solvent. Alternatively, the reaction may conveniently be effected in an inert solvent such as, for example, an acyclic ether (e.g. diethyl ether or diglyme); a cyclic ether (e.g. dioxan or tetrahydrofuran); an amide (e.g. N,N-dimethylformamide or N,N-dimethylacetamide); an optionally halogenated hydrocarbon (e.g. dichloromethane); an alcohol (e.g. methanol or ethanol); a ketone (e.g. acetone or methylisobutylketone); or an ester (e.g. ethyl acetate); or in a mixture of two or more such solvents. The methylation reaction described above may be performed either before or after reduction of the sulphoxide function of the compound of formula (IV) initially obtained.

Reduction of a compound of formula (IIIA), or a salt thereof, to the corresponding sulphide may be effected by any convenient means. For example, reduction may be effected by initially preparing the corresponding acyloxysulphonium or alkoxysulphonium salt in situ by reaction of the compound of formula (IIIA) or a salt thereof with e.g. acetyl chloride (in the case of an acetoxysulphonium salt). Reduction of the acyloxysulphonium or alkyloxysulphonium salt may be effected by, for example, reaction with sodium dithionite or, more preferably, with iodide ion, for example using a solution of potassium iodide in a solvent such as acetic acid, acetone, tetrahydrofuran, dioxan, dimethylformamide or dimethylacetamide. A preferred solvent for this reaction is acetone. The reaction may be effected at a temperature from −20° to +50° C., preferably from about 0° C. to 25° C.

It will be appreciated that in processes for the preparation of compounds of formula (I) it will in many instances be necessary to protect the carboxyl group(s), for example using a carboxyl blocking group. Carboxyl blocking groups used in the preparation of compounds of formula (I) or in the preparation of necessary starting materials are desirably groups which may readily be split off at a suitable stage in the reaction sequence, conveniently at the last stage. It may, however, be convenient in some instances to employ biologically acceptable, metabolically labile carboxyl blocking groups such as acyloxymethyl groups (e.g. a pivaloyloxymethyl group) and retain these in the final product to give a biologically acceptable ester derivative of a compound of formula (I).

Suitable carboxyl blocking groups are well known in the art, a list of representative blocked carboxyl groups being included in British Patent Specification No. 1399086.

The carboxyl blocking group may be, for example, the residue of an ester-forming aliphatic or araliphatic alcohol or an ester-forming phenol, silanol or stannanol preferably containing 1-20 carbon atoms. Thus, carboxyl blocking groups which may conveniently be employed include aryl lower alkyl groups, such as p-methoxybenzyl, p-nitrobenzyl and diphenylmethyl; lower alkyl groups such as t-butyl; lower haloalkyl groups such as 2,2,2-trichloroethyl and tri(lower alkyl)-silyl groups such as trimethylsilyl.

Amino protecting groups suitable for use in the preparation of compounds of formula (I) or in the preparation of necessary starting materials are desirably groups which may readily be split off at a suitable stage in the reaction sequence, conveniently at the last stage. Amino protecting groups may be chosen from groups conventionally used in the art, for example, aralkyl groups such as triphenylmethyl, or acyl groups such as chloroacetyl, formyl, t-butoxycarbonyl, 2,2,2-trichloroethoxycarbonyl or isoamyloxycarbonyl.

Any carboxyl blocking or amino protecting groups employed in the preparation of compounds of formula (I) may be removed if desired, by any appropriate methods known in the art. Suitable methods for removing carboxyl blocking groups include acid hydrolysis and reduction. Thus, for example diphenylmethyl and t-butyl carboxyl blocking groups may conveniently be removed by acid hydrolysis. A p-nitrobenzyl group may conveniently be cleaved by reduction, effected for example by zinc and acetic acid, conveniently in the presence of a water-miscible solvent such as acetone, tetrahydrofuran, dioxan, dimethylformamide or dimethylacetamide. Where it is desired to remove a carboxyl blocking group from a quaternary compound of formula (III), or the corresponding sulphide, having an associated anion, the anion is preferably not a halide. A halide salt may be converted to a non-halide salt e.g. a trifluoroacetate salt, by conventional methods, prior to deprotection.

Methods of removing amino protecting groups are also well known in the art. A trityl group may for example be removed using an optionally halogenated carboxylic acid e.g. acetic acid, formic acid, chloroacetic acid or trifluoroacetic acid or using a mineral acid, e.g. hydrochloric acid, or mixtures of such acids, preferably in the presence of a protic solvent such as water. Acid-labile acyl amino-protecting groups, e.g. formyl, t-butoxycarbonyl or isoamyloxycarbonyl may also be removed, where appropriate under the conditions described above for a trityl group. A chloroacetyl group may be removed by treatment with thiourea. Other acyl amino-protecting groups e.g. 2,2,2-trichloroethoxycarbonyl may be removed, for example, by reduction.

It will be appreciated that the use of amino protecting and carboxyl blocking groups is well known in the art. Relevant examples of such use are given in e.g. Theodora W. Greene "Protective Groups in Organic Synthesis" (Wiley-Interscience, New York 1981), and J. P. W. McOmie, "Protective Groups in Organic Chemistry" (Plenum Press, London 1973).

The compounds of formula (I) and their non-toxic derivatives (as herein defined) may if desired be isolated as solvates (e.g. hydrates), for example by conventional methods.

Where a compound of formula (I) is obtained as a mixture of syn and anti isomers, the syn isomer may be obtained by, for example, conventional methods such as crystallisation or chromatography.

According to a preferred embodiment of the invention, the preparation of 7-[(Z)-2-methoxyimino-2-(2-aminothiazol-4-yl)acetamido]-3-[(1-methyl-1-pyrrolidinium)methyl]-ceph-3-em-4-carboxylate is effected by reaction of a compound of formula (II) wherein $R^{2a}$ is a methyl group, in N-protected and carboxyl blocked form, with N-methylpyrrolidine to give a corresponding compound of formula (IIIA) in protected form which is then reduced to the corresponding sulphide and protecting and blocking groups are finally removed.

Starting materials of formula (II) may, for example, be prepared by oxidising a compound of formula (V)

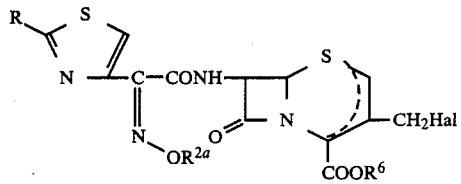

(wherein R, $R^{2a}$, $R^6$ and Hal are hereinbefore defined and the dotted line bridging the 2, 3 and 4 positions indicates that the compound is a ceph-2-em or a ceph-3-em compound) or a salt thereof. Conventional oxidising agents may be used, for example percarboxylic acids such as m-chloroperbenzoic acid, trifluoroperacetic acid or performic acid in a non-aqueous solvent (e.g. a halogenated hydrocarbon such as methylene chloride). Conveniently the oxidation will be performed at temperatures below ambient temperature (e.g. at or around 0° C.) to prevent sulfone formation.

The products of the oxidation reaction are generally obtained as a mixture of epimeric R and S sulfoxides in which the S isomer normally greatly predominates. Separation of the epimers may be performed in a conventional manner, if desired. However, in general, separation of epimers is not necessary, since the desired sulphide cephalosporins, prepared by the subsequent reduction of the sulphoxide cephalosporins, do not retain the asymmetric sulphur centre. It will be appreciated that the oxides of formulae (II) and (IIIA), may be employed either in the S or R form or as a mixture of epimers.

When a ceph-2-em compound of formula (V) is employed in the oxidation this will be isomerised under the reaction conditions to yield the corresponding ceph-3-em 1-oxide.

According to a further feature of the present invention, there are provided compounds of formula (I) as hereinbefore defined and non-toxic pharmaceutically acceptable salts and metabolically labile esters thereof and solvates of these compounds when prepared by a process as herein described.

The following non-limiting Example is intended to provide further illustration of the invention. All temperatures are in °C. DMSO is dimethylsulphoxide. Sorbsil U30 is silica gel manufactured by Joseph Crosfield and Son of Warrington, Cheshire, England.

EXAMPLE (a) Diphenylmethyl (6R,7R,2'Z)-3-Bromomethyl-7-[2-methoxyimino-2-(2-triphenylmethylamino-4-thiazolyl) acetamido]ceph-3-em-4-carboxylate.

Oxalyl chloride (3.2 ml) was added to a solution of dimethyformamide (3.3 ml) with stirring under nitrogen in methylene chloride (80 ml) at −20°. The mixture was stirred with ice-water cooling for 10 minutes and then recooled to −20°. (Z)-2-Methoxyimino-2-(2-triphenylmethylamino-4-thiazolyl)acetic acid (15.36 g) was added. The solution was stirred with ice-water cooling for 10 minutes before recooling to −20°. A slurry of diphenylmethyl (6R,7R)-7-amino-3-bromomethylceph-3-em-4-carboxylate, hydrochloride (17.2 g) in methylene chloride (80 ml) containing dimethylaniline (15.3ml) was added and the mixture was allowed to warm to 21° over 30 minutes. The solution was washed with dilute hydrochloric acid and twice with water. The washings were extracted with methylene chloride. The combined organic layers were dried with magnesium sulphate and concentrated. The solution was loaded onto a column of Sorbsil U30 (250 g) set up in methylene chloride. The column was eluted with methylene chloride and 10% ethyl acetate in methylene chloride to give the title compound (22.06 g); $[\alpha]_D^{21} -5.2°$ (c=1.5, chloroform); $\nu_{max \, (bromoform)}$, 3400 (NH), 1792 (β-lactam), 1730 (ester) and 1684 and 1518 cm$^{-1}$ (amide).

(b) Diphenylmethyl (1S,6R,7R,2′Z)-3-Bromomethyl-7-[2-methoxyimino-7-(2-triphenylmethylamino-4-thiazolyl)acetamido]-ceph-3-em-4-carboxylate 1-oxide The product of stage (a) (16 g) was stirred with m-chloroperbenzoic acid (3.75 g) in methylene chloride (400 ml) with ice-water cooling. After 15 minutes the solution was washed with aqueous sodium carbonate solution and water and the washings were extracted with methylene chloride. The combined organic solution were dried with magnesium sulphate. The solution was concentrated and loaded onto a column of Sorbsil U30 (200 g) set up in methylene chloride. The column was eluted with methylene chloride, then 20% ethyl acetate in methylene chloride to give the title compound (14.4 g); $[\alpha]_D^{21} 9.92°$ (c=1.2, chloroform); $\nu_{max}$ (bromoform), 3350 (NH), 1809 (β-lactam), 1731 (ester), 1686 and 1518 (amide) and 1048 cm$^{-1}$ (sulphoxide).

(c) Diphenylmethyl (1S,6R,7R,2′Z)-7-[2-Methoxyimino-2-(2-triphenylmethylamino-4-thiazolyl)acetamido]-3-[(1-methyl-1-pyrrolidinium)methyl]-ceph-3-em-4-carboxylate 1-oxide, bromide The product of stage (b) (11.67 g) was stirred with N-methylpyrrolidine (1.75ml) in tetrahydrofuran (200ml) at 21° for 2 hours. The mixture was diluted with diethyl ether (800 ml) and the precipitate was collected by filtration, washed with diethyl ether and dried to give a solid (10 g). The solid was dissolved in methylene chloride and loaded on a column of Sorbsil U30 (250 g) set up in ethyl acetate. The column was eluted successively with ethyl acetate and methanol (10 to 60%) in ethyl acetate. The appropriate eluate was evaporated to dryness and the residue was triturated with diethyl ether to give the title comoound (5.0 g); $[\alpha]_D^{21} 8.66°$ (c=1.15, DMSO); $\nu_{max}$ (bromoform), 3390 (NH), 1806 (β-lactam), 1728 (ester), 1690 and 1518 (amide) and 1045 cm$^{-1}$ (sulphoxide).

(d) Diphenylmethyl (6R,7R,2′Z)-7-[2-Methoxyimino-2-(2-triphenylmethylamino-4-thiazolyl)acetamido]-3-(1-methyl-1-pyrrolidinium)methyl]-ceph-3-em-4-carboxylate, iodide The product of stage (c) (7.55 g) was stirred with acetone (200 ml) at 20° until most of the solid had dissolved. The mixture was cooled with ice-water and finely ground potassium iodide (6.36 g) was added. After ten minutes, acetyl chloride (0.58 ml) was added. Further portions of acetyl chloride (0.58 ml) were added after 40 minutes and 1 hour 10 minutes. The cooling bath was then removed. Further acetyl chloride (0.58 ml portions) was added after 1 hour 40 minutes and 2 hours 10 minutes After 3.5 hours, further potassium iodide (3 g) and acetyl chloride (0.58 ml) were added. After five hours, the reaction mixture was poured into aqueous sodium metabisulphite solution and the product was extracted twice with methylene chloride The combined organic layers were washed with water three times and the solution dried with magnesium sulphate. The solution was evaporated to a gum which was triturated with ethyl acetate to give the title compound (5.28 g);$[\alpha]_D^{21} -15.4°$ (c=0.42, DMSO); $\nu_{max}$ (Nujol), 3700–2500 (NH+H$_2$O), 1788 (β-lactam), 1728 (ester) and 1678 and 1525 cm$^{-1}$ (amide).

(e) (6R,7R,2′Z)-7-[2-(2-Amino-4-thiazolyl)-2-methoxyimino-acetamido]-3-[(1-methyl-1-pyrrolidinium)methyl]-ceph-3-em-4-carboxylate, hydroiodide The product of stage (d) (4.64 g) was dissolved in formic acid (35 ml) and water (15 ml) was added with stirring at 21°. The solution was stirred at 50° for one hour and then cooled at 21°. The mixture was filtered and the filter-cake was leached with 70% formic acid. The combined filtrates were evaporated and the residue was triturated with acetone to give the title comoound (2.49 g); $[\alpha]_D^{21} 14.4°$ (c=1.0, DMSO); $\nu_{max}$ (Nujol) 3700–2100 (NH, NH$_3^+$, H$_2$O), 1787 (β-lactam), 1674 and 1533 (amide) and 1623 cm$^{-1}$ (carboxylate).

I claim:

1. A process for the preparation of a compound of formula (I)

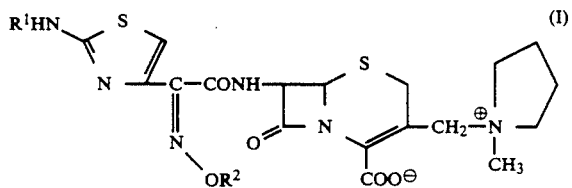

wherein

R$^1$ is a hydrogen atom or an amino-protecting group; and

R$^2$ is a straight or branched chain C$_{1-4}$ alkyl group, an allyl, but-2-enyl or but-3-enyl group, or is a group of formula

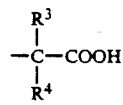

wherein each of R$^3$ and R$^4$ is independently a hydrogen atom or a methyl or ethyl group, or R$^3$ and R$^4$ taken together with the carbon atom to which they are attached may be a C$_{3-5}$ cycloalkylidene group, or a nontoxic pharmaceutically acceptable salt or a metabolically labile ester thereof or a solvate of such a compound, which process comprises reducing a compound of formula (IIIA)

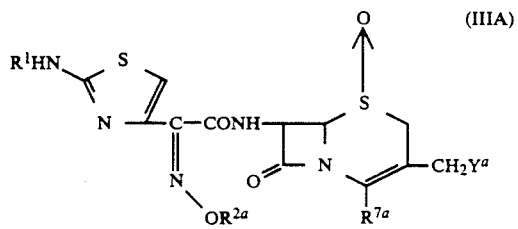

wherein R$^1$ is a hydrogen atom or an amino protective group; R$^{2a}$ is a straight or branched chain C$_{1-4}$ alkyl group, an allyl, but-2-enyl, or but-3-enyl group, or is a group of formula

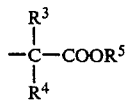

wherein each of $R^3$ and $R^4$ is independently a hydrogen atom or a methyl or ethyl group, or $R^3$ and $R^4$ taken together with a carbon atom to which they are attached may be a $C_{3-5}$ cycloalkylidene group, and $R^5$ is a hydrogen atom or carboxyl blocking group;

$Y^a$ is a 1-pyrrolidino or 1-methyl-1-pyrrolidinium group, and $R^{7a}$ represents the group —COOR$^6$, where $R^6$ is a hydrogen atom or a carboxyl blocking group, or when $Y^a$ represents 1-methyl-1-pyrrolidinum, $R^{7a}$ may additionally represent the group —COO, or a salt thereof to form the corresponding sulphide compound; and if necessary or desired:

(a) methylation of a 3-(1-pyrrolidino)methyl compound to form the corresponding 3-(1-methyl-1-pyrrolidinium)-methyl compound;

(b) formation of a non-toxic salt or a non-toxic metabolically labile ester; and (c) removal of any carboxyl blocking and amino protecting groups.

2. A process as claimed in claim 1, wherein a corresponding acyloxysulphonium or alkoxysulphonium salt is initially prepared in situ, after which said salt is reduced.

3. A process as claimed in claim 1 wherein $R^{7a}$ is the group —COOR$^6$, and $R^6$ and $R^5$, if present, are carboxyl blocking groups selected from acyl lower alkyl groups, lower haloalkyl groups and tri(lower alkyl)silyl groups.

4. A process as claimed in claim 1 which comprises the step of preparation of the starting compound of formula (IIIA) or a salt thereof by a process which comprises reacting a compound of formula II

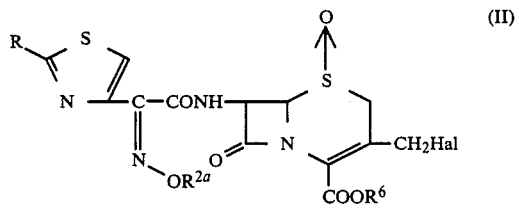

wherein R is an amino or protected amino group;

$R^{2a}$ is a straight or branched chain $C_{1-4}$ alkyl group, an allyl, but-2-enyl or but-3-enyl group, or is a group of formula

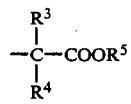

wherein each of $R^3$ and $R^4$ is independently a hydrogen atom or a methyl or ethyl group, or $R^3$ and $R^4$ taken together with the carbon atom to which they are attached may be a $C_{3-5}$ cycloalkylidene group, and $R^5$ is a hydrogen atom or a carboxyl blocking group; $R^6$ is a hydrogen atom or a carboxyl blocking group; and Hal is a halogen atom, or a salt thereof with pyrrolidene or N-methylpyrrolidene followed, when pyrrolidene is used, by reaction with a methylating agent.

5. A process, as claimed in claim 4 in which (1S,6R,7R,2'Z)-3-bromoethyl-7-[2-methoxyimino-7-(2-amino-4-thiazolyl)-acetamido]-ceph-3-em-4-carboxylate 1-oxide in N-protected and carboxyl blocked form is reacted with N-methylpyrrolidene and the initial product of formula (IIIA) is subjected to reduction to the corresponding sulphide followed by removal of N-protecting and carboxyl blocking groups to yield (6R,7R,2'Z)-7-[(Z)-2-methoxyimino-2-(2-aminothiazol-4-yl)acetamido]-3-[(1-methyl-1-pyrrolidinium)methyl]-ceph-3-em-4-carboxylate.

6. A process as claimed in claim 1 wherein $R^1$ is an amino protecting group selected from aralkyl and acyl groups.

* * * * *